US012616231B2

(12) United States Patent
Sakai

(10) Patent No.: US 12,616,231 B2
(45) Date of Patent: May 5, 2026

(54) HEAT COAGULATION GEL STRENGTH REGULATING AGENT FOR EGG WHITE PROTEIN

(71) Applicant: AMANO ENZYME INC., Nagoya (JP)

(72) Inventor: Kiyota Sakai, Kakamigahara (JP)

(73) Assignee: Amano Enzyme Inc., Nagoya (JP)

( * ) Notice: Subject to any disclaimer, the term of this patent is extended or adjusted under 35 U.S.C. 154(b) by 315 days.

(21) Appl. No.: 18/254,697

(22) PCT Filed: Nov. 25, 2021

(86) PCT No.: PCT/JP2021/043190
§ 371 (c)(1),
(2) Date: May 26, 2023

(87) PCT Pub. No.: WO2022/114059
PCT Pub. Date: Jun. 2, 2022

(65) Prior Publication Data
US 2024/0008515 A1     Jan. 11, 2024

(30) Foreign Application Priority Data
Nov. 27, 2020    (JP) ................................. 2020-197201

(51) Int. Cl.
*A23L 29/20*        (2016.01)
*A23L 15/00*        (2016.01)
*C12N 9/80*         (2006.01)
(52) U.S. Cl.
CPC ............... *A23L 29/20* (2016.08); *A23L 15/25* (2016.08); *C12N 9/80* (2013.01); *C12Y 305/01044* (2013.01)

(58) Field of Classification Search
CPC ........... A23L 29/20; A23L 15/25; C12N 9/80; C12Y 305/01044
USPC ......................................................... 426/32
See application file for complete search history.

(56) References Cited

U.S. PATENT DOCUMENTS

| | | | |
|---|---|---|---|
| 6,756,221 | B1 | 6/2004 | Yamaguchi |
| 2004/0072318 | A1 | 4/2004 | Yamaguchi et al. |
| 2004/0166558 | A1 | 8/2004 | Yamaguchi et al. |
| 2004/0175799 | A1 | 9/2004 | Yamaguchi |
| 2007/0254065 | A1 | 11/2007 | Kodera et al. |

(Continued)

FOREIGN PATENT DOCUMENTS

| | | |
|---|---|---|
| CN | 106942459 A | 7/2017 |
| JP | H07-079707 A | 3/1995 |

(Continued)

OTHER PUBLICATIONS

International Search Report in International Application No. PCT/JP2021/043190, mailed on Feb. 8, 2022.

(Continued)

*Primary Examiner* — Brent T O'Hern
(74) *Attorney, Agent, or Firm* — Knobbe, Martens, Olson & Bear, LLP

(57) ABSTRACT

The purpose of the present invention is to provide a technology that enables control for increasing or decreasing the heat coagulation gel strength of egg white protein, and that has little effect on taste. This heat coagulation gel strength regulating agent for egg white protein contains a protein deamidase and can control the increase or decrease of the heat coagulation gel strength of egg white protein.

4 Claims, 1 Drawing Sheet

(56)                    References Cited

U.S. PATENT DOCUMENTS

| | | |
|---|---|---|
| 2009/0061500 A1 | 3/2009 | Yamaguchi |
| 2009/0075337 A1 | 3/2009 | Yamaguchi |
| 2009/0081763 A1 | 3/2009 | Yamaguchi |
| 2017/0044513 A1* | 2/2017 | Yokoyama ............. A23C 13/16 |

FOREIGN PATENT DOCUMENTS

| | | | |
|---|---|---|---|
| JP | H07250651 A * | 10/1995 | |
| JP | 2000-050887 A | 2/2000 | |
| JP | 2001-218590 A | 8/2001 | |
| JP | 2017-175976 A | 10/2017 | |
| WO | WO 2006/075772 A1 | 7/2006 | |

OTHER PUBLICATIONS

International Preliminary Report on Patentability in International Application No. PCT/JP2021/043190, mailed on May 30, 2023.

Yamaguchi et al., "Technology for the Development of Novel Food Enzyme, Protein-Glutaminase, and Its Application in Food Industry". Food Chemicals, vol. 24, No. 12, 2008, pp. 62-65 p. 64, Figure 1.

Hiroko et al., "Thermal Coagulation of Egg White and Egg Yolk; Effects of Salt and Sugar". Journal of Cookery Science of Japan, vol. 15, No. 2 (1982), pp. 114-118.

Extended European Search Report for EP Appl. No. 21898031.6 dated Dec. 17, 2024 (in 9 pages).

Japanese Office Action issued for Japanese App. No. 2022-565406, dated Jul. 29, 2025 (in 14 pages).

Kitabatake, N. & Doi, E. "Improvement of protein gel by physical and enzymatic treatment", Food Reviews International, 9(4), 1993, pp. 445-471.

Nakamura, R. in Science of Food, *"The Science of Eggs"*, First Edition, First Printing, Jan. 25, 1998, pp. 79-86.

* cited by examiner

HEAT COAGULATION GEL STRENGTH REGULATING AGENT FOR EGG WHITE PROTEIN

TECHNICAL FIELD

The present invention relates to a strength-adjusting agent for a gel to be obtained by thermal coagulation of an egg white protein.

BACKGROUND ART

An egg white protein has a property of forming a gel network by thermal coagulation, and this property is an important factor for determination of a texture characteristic of a food cooked using egg white.

For cooking of an egg, a technique has been reported that enables use of an original coagulation property of an egg and, in addition, enables modification of an obtained cooked food. For example, Patent Document 1 shows that the tissue of an egg processed food can be densified by adding transglutaminase to a raw material mainly containing an egg and then cooking the raw material. Patent Document 2 shows that when an egg processed food such as a boiled egg is immersed in a solution containing transglutaminase, hardness and elasticity can be imparted to the egg processed food as compared with the case of treatment with no transglutaminase.

A study on coagulation properties of eggs has reported that the jelly strength is increased by adding salt and decreased by adding sugar.

PRIOR ART DOCUMENTS

Patent Documents

Patent Document 1: Japanese Patent Laid-open Publication No. 7-250651

Patent Document 2: Japanese Patent Laid-open Publication No. 2017-175976

Non-Patent Document

Non-Patent Document 1: Journal of Cookery Science of Japan Vol. 15, No. 2, (1982) p. 114-118

SUMMARY OF THE INVENTION

Problems to be Solved by the Invention

Thermal coagulation properties of the egg white protein are used in a wide range of cooked foods, and therefore it is considered that the versatility of the egg white protein can be further expanded if an increase/decrease (increase or decrease) of the strength of a gel to be obtained by thermal coagulation of the egg white protein can be controlled by a method without significant influence on the taste. However, a method using transglutaminase as in Patent Documents 1 and 2 is expected to have only an effect from an enzyme property of catalyzing a protein crosslinking reaction, that is, only an effect of increasing the strength of a gel to be obtained by thermal coagulation of the egg white protein, and a method using a condiment such as salt or sugar as in Non-Patent Document 1 has a large influence on the taste, thus resulting in a limited range of application in cooked foods.

Therefore, an object of the present invention is to provide a technique that enables control of an increase/decrease (increase or decrease) of the strength of a gel to be obtained by thermal coagulation of the egg white protein and has a small influence on the taste.

Means for Solving the Problem

As a result of intensive studies, the present inventor has unexpectedly found that a protein deamidase (protein-glutaminase) can exhibit both effects of increasing and decreasing the strength of a gel to be obtained by thermal coagulation of the egg white protein according to the amount of the protein deamidase added. The present invention has been completed by further studies based on the above-described finding. That is, the present invention provides the invention of the aspects described below.

Item 1. A strength-adjusting agent for a gel to be obtained by thermal coagulation of an egg white protein, the strength-adjusting agent including a protein deamidase.

Item 2. The strength-adjusting agent for a gel to be obtained by thermal coagulation according to the item 1, to be used for producing a food containing a gel obtained by thermal coagulation of an egg white protein.

Item 3. The strength-adjusting agent for a gel to be obtained by thermal coagulation according to the item 1 or 2, wherein the protein deamidase is used in an amount of 0.1 to 19 U with respect to 1 g of the egg white protein, the strength-adjusting agent is to be used for increasing a strength of a gel to be obtained by thermal coagulation of an egg white protein.

Item 4. The strength-adjusting agent for a gel to be obtained by thermal coagulation according to the item 1 or 2, wherein the protein deamidase is used in an amount of 20 U or more with respect to 1 g of the egg white protein, the strength-adjusting agent is to be used for decreasing a strength of a gel to be obtained by thermal coagulation of an egg white protein.

Item 5. A method for adjusting a strength of a gel obtained by thermal coagulation of an egg white protein, the method including:

a step 1 of treating an egg white protein with a protein deamidase; and a step 2 of thermally coagulating the egg white protein treated.

Item 6. A method for producing a material for gelation, the method including a step of treating a material containing an egg white protein using a strength-adjusting agent for a gel to be obtained by thermal coagulation of an egg white protein, the strength-adjusting agent including a protein deamidase, to obtain a material for gelation in which a strength of a gel to be obtained by thermal coagulation is adjusted.

Item 7. A method for producing a food, the method including a step of heating and coagulating the material for gelation obtained by the method according to the item 6.

Item 8. A method for producing a food, the method including the steps of:

preparing a mixture of the material for gelation obtained by the method according to the item 6 and another food material; and heating the mixture at a temperature at which the material for gelation is coagulated by heating.

Advantages of the Invention

According to the present invention, a technique is provided that enables control of an increase/decrease (increase or decrease) of the strength of a gel to be obtained by thermal coagulation of the egg white protein and has a small influence on the taste.

BRIEF DESCRIPTION OF THE SEVERAL VIEWS OF THE DRAWING(S)

EMBODIMENTS OF THE INVENTION

Figure 1:
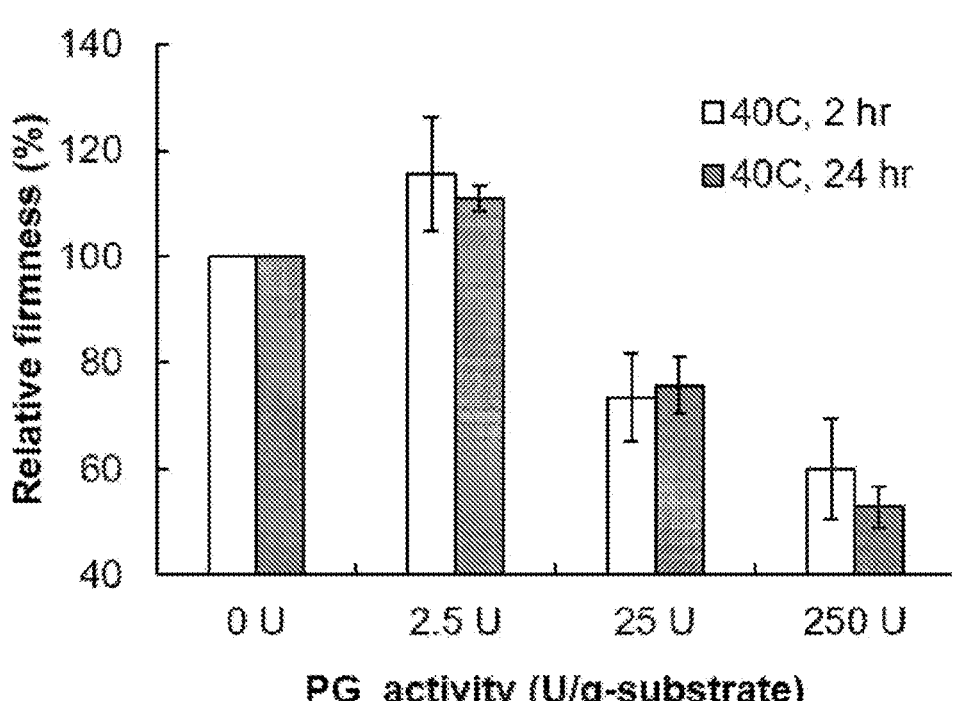
FIG. 1 shows results of adjusting the strength of a gel obtained by thermal coagulation of an egg albumin diluted at a dilution rate of 5 w/v % and subjected to a PG treatment.

1. Strength-Adjusting Agent for Gel to be Obtained by Thermal Coagulation of Egg White Protein The strength-adjusting agent for a gel to be obtained by thermal coagulation of an egg white protein of the present invention includes a protein deamidase.

1-1. Active Component

The protein deamidase is included as an active component in the strength-adjusting agent for a gel to be obtained by thermal coagulation of an egg white protein of the present invention. The type, the origin, and the like of the protein deamidase are not particularly limited as long as the enzyme exhibits an action of decomposing an amide group-containing side chain of a protein without cleavage of a peptide bond and crosslinking of the protein. Examples of the protein deamidase include protein deamidases derived from the genera *Chryseobacterium, Flavobacterium, Empedobacter, Sphingobacterium, Aureobacterium*, and *Myroides* disclosed in JP 2000-50887 A, JP 2001-218590 A, and WO 2006/075772 A1 and commercially available products of protein-glutaminases derived from the genus *Chryseobacterium*. These protein deamidases may be used singly or in combination of two or more thereof.

Among these protein deamidases, protein deamidases derived from the genus *Chryseobacterium* are preferable, protein-glutaminases derived from the genus *Chryseobacterium* are more preferable, and protein-glutaminases derived from *Chryseobacterium proteolyticum* are still more preferable from the viewpoint of further enhancing the effect of adjusting the strength of a gel to be obtained by thermal coagulation of an egg white protein.

The protein deamidase can be prepared from a culture liquid of a microorganism as an origin of the protein deamidase. Specific examples of the preparation method include a method in which the protein deamidase is recovered from a culture liquid or a bacterial cell of the above-described microorganism. For example, in the case of using a microorganism that secretes a protein deamidase, a bacterial cell is previously recovered from a culture liquid by, as necessary, filtration, centrifugation, or the like, and then an enzyme can be separated and/or purified. In the case of using a microorganism that secretes no protein deamidase, a bacterial cell is previously recovered from a culture liquid as necessary and then disrupted by pressure treatment, ultrasonic treatment, or the like to expose an enzyme, and then the enzyme can be separated and/or purified. As the method of separation and/or purification of an enzyme, a known method of separation and/or purification of a protein can be used without particular limitation, and examples of the method include a centrifugal separation method, an ultrafiltration (UF) concentration method, a salting-out method, and various chromatography methods using an ion exchange resin and the like. The separated and/or purified enzyme can be powderized with a drying method such as freeze-drying, reduced-pressure drying, or spray drying and can also be powderized using an appropriate excipient and/or drying aid in the drying method. The separated and/or purified enzyme can also be liquefied by addition of an appropriate additive and filtration sterilization.

As the protein deamidase, a commercially available product can also be used, and examples of a preferred commercially available product include a protein-glutaminase "Amano" 500 manufactured by Amano Enzyme Inc.

The content of the protein deamidase in the strength-adjusting agent for a gel to be obtained by thermal coagulation of an egg white protein of the present invention is not particularly limited, and is, for example, 0.1 to 10,000 U/g, preferably 1 to 8,000 U/g, 10 to 6,000 U/g, 50 to 4,000 U/g, 100 to 2,000 U/g, 150 to 1,000 U/g, or 200 to 800 U/g, more preferably 300 to 700 U/g, still more preferably 400 to 600 U/g, and still even more preferably 450 to 550 U/g.

The activity of the protein deamidase is defined so that when benzyloxycarbonyl-L-glutaminylglycine (Z-Gln-Gly) is used as a substrate, the amount of enzyme that liberates 1 μmol of ammonia per minute is 1 unit (1 U).

1-2. Another Component

The strength-adjusting agent for a gel to be obtained by thermal coagulation of an egg white protein of the present invention may include another component in addition to the protein deamidase to an extent such that an effect of the present invention is not affected. Examples of another component include enzymes other than the predetermined protein-glutaminases, and additives.

Examples of the enzymes other than the predetermined protein-glutaminases include amylases (α-amylases, β-amylases, glucoamylases), glucosidases (α-glucosidases, β-glucosidases), galactosidases (α-galactosidases, β-galactosidases), proteases (acidic proteases, neutral proteases, alkaline proteases), peptidases (leucine peptidases, aminopeptidases), lipases, esterases, cellulases, phosphatases (acidic phosphatases, alkaline phosphatases), nucleases, deaminases, oxidases, dehydrogenases, glutaminases, pectinases, catalases, dextranases, transglutaminases, and pullulanases. These enzymes may be included singly or in combination of two or more thereof.

Examples of the additives include excipients, buffers, suspending agents, stabilizers, preservatives, antiseptics, and physiological saline. Examples of the excipients include starch, dextrin, maltose, trehalose, lactose, D-glucose, sorbitol, D-mannitol, sucrose, and glycerol. Examples of the buffers include phosphates, citrates, and acetates. Examples of the stabilizers include propylene glycol and ascorbic acid. Examples of the preservatives include phenol, benzalkonium chloride, benzyl alcohol, chlorobutanol, and methylparaben. Examples of the antiseptics include ethanol, benzalkonium chloride, parahydroxybenzoic acid, and chlorobutanol. These additives may be included singly or in combination of two or more thereof.

1-3. Preparation Form

The form of the strength-adjusting agent for a gel to be obtained by thermal coagulation of an egg white protein of the present invention is not particularly limited, and examples of the form include forms of liquids and solids (such as powders and granules). Preparation into these forms is to be performed with a generally known method.

1-4. Intended Use

The strength-adjusting agent for a gel to be obtained by thermal coagulation of an egg white protein of the present invention is used for the purpose of increasing or decreasing the gel strength of a gel generated by thermal coagulation of an egg white protein. Specifically, the strength-adjusting agent for a gel to be obtained by thermal coagulation of an egg white protein of the present invention can be used as an agent capable of providing a protein deamidase that treats an egg white protein in a method, for adjusting a strength of a gel obtained by thermal coagulation of an egg white protein, including a step 1 of treating an egg white protein with a protein deamidase and a step 2 of thermally coagulating the egg white protein treated.

The egg white protein is not particularly limited as long as it is an egg white protein of a bird's egg, and is preferably a bird's edible egg, and more preferably an egg white protein of a hen's egg. The egg white protein is not particularly limited as long as it is a protein included in egg white, and examples of the egg white protein include ovalbumin, ovotransferrin, ovomucoid, and ovomucin, and these egg white proteins may be used singly or in combination of two or more thereof. Among these egg white proteins, at least ovalbumin is preferably included from the viewpoint of further enhancing the effect of adjusting the strength of a gel obtained by thermal coagulation of an egg white protein.

The specific form of the egg white protein in the step 1 is not particularly limited as long as the form includes an egg white protein that is not coagulated by heating, and examples of the form include forms of purified egg white proteins, raw egg white, dried egg white, raw whole eggs, dried whole eggs, and mixtures of these with other components (such as other food ingredients).

The dilution rate of the egg white protein in the step 1 is not particularly limited, and is, for example, 0.1 to 30 w/v %, preferably 0.3 to 25 w/v %, more preferably 0.6 to 20 w/v %, still more preferably 1 to 15 w/v %, and still even more preferably 3 to 12 w/v %.

The control of an increase or decrease of the gel strength of a gel generated by thermal coagulation of an egg white protein with the strength-adjusting agent for a gel to be obtained by thermal coagulation of an egg white protein of the present invention can be performed by adjusting the amount of the protein deamidase used with respect to the amount of the egg white protein in the step 1. For example, in the case of increasing the gel strength of a gel generated by thermal coagulation of an egg white protein, the amount of the protein deamidase used with respect to the amount of the egg white protein can be made relatively small, and in the case of decreasing the gel strength of a gel generated by thermal coagulation of an egg white protein, the amount of the protein deamidase used with respect to the amount of the egg white protein can be made relatively large.

More specifically, in the case of increasing the gel strength of a gel generated by thermal coagulation of an egg white protein, the amount of the protein deamidase used with respect to 1 g of the egg white protein is, for example, 0.1 to 19 U, preferably 0.25 to 15 U, 0.5 to 11 U, 0.75 to 7.5 U, or 1 to 4 U, more preferably 1.5 to 3.5 U, still more preferably 2 to 3 U, and still even more preferably 2.2 to 2.8 U.

In the case of decreasing the gel strength of a gel generated by thermal coagulation of an egg white protein, the amount of the protein deamidase used with respect to 1 g of the egg white protein can be further increased, and is, for example, 5 U or more or 10 U or more, preferably 15 U or more or 20 U or more, more preferably 25 U or more, still more preferably 50 U or more, even more preferably 100 U or more, and still even more preferably 200 U or more. In this case, the upper limit of the amount range of the protein deamidase used with respect to 1 g of the egg white protein is not particularly limited, and is, for example, 500 U or less, 400 U or less, 300 U or less, or 260 U or less.

The protein deamidase treatment temperature in the step 1 is not particularly limited as long as it is lower than the thermal coagulation temperature of the egg white protein, and can be appropriately determined by those skilled in the art on the basis of, for example, the optimal temperature of the protein deamidase, and is preferably 35 to 65° C., 35 to 60° C., or 35 to 59° C., more preferably 36 to 55° C., still more preferably 37 to 55° C., even more preferably 38 to 50° C., and still even more preferably 39 to 45° C.

The protein deamidase treatment time in the step 1 is not particularly limited, and is to be appropriately determined according to, for example, the scale of the amount of the composition to be treated, and is, for example, 0.5 hours or more, preferably 1 hour or more, more preferably 1.5 hours or more, still more preferably 2 hours or more, 8 hours or more, 12 hours or more, or 20 hours or more. The upper limit of the range of the protein deamidase treatment time is not particularly limited, and is, for example, 30 hours or less, 24 hours or less, 12 hours or less, 8 hours or less, 6 hours or less, or 4 hours or less.

The treatment temperature in the step 2 is not particularly limited as long as the egg white protein can be thermally coagulated at the temperature. The treatment temperature is to be appropriately determined according to the type of the egg white protein to be treated, and is, for example, 60° C. or higher, preferably 65° C. or higher, more preferably 70° C. or higher, still more preferably 75° C. or higher, and still even more preferably 78° C. or higher. The upper limit of the treatment temperature range is not particularly limited as long as a gel of the thermally coagulated egg white protein can be obtained, and the upper limit can be appropriately determined by those skilled in the art according to the form of the egg white protein. For example, in a case where the strength-adjusting agent for a gel to be obtained by thermal coagulation of an egg white protein of the present invention is used for producing a food as described below, the treatment can be performed at a normal heating temperature for cooking of the food.

As described above, the strength-adjusting agent for a gel to be obtained by thermal coagulation of an egg white protein of the present invention can increase or decrease the strength of a gel to be obtained by thermal coagulation of an egg white protein, and thus can vary the texture characteristics of a food cooked using an egg white protein. Therefore, the strength-adjusting agent for a gel to be obtained by thermal coagulation of an egg white protein of the present invention can be preferably used for producing a food containing a gel obtained by thermal coagulation of an egg white protein.

The food containing a gel obtained by thermal coagulation of an egg white protein is not particularly limited as long as the food is obtained by cooking using egg white, and a non-emulsified food is preferable from the viewpoint of further enhancing the effect of adjusting the strength of a gel obtained by thermal coagulation of an egg white protein. More specific examples of the food include cooked egg foods (such as boiled eggs, hot-spring eggs, poached eggs, scrambled eggs, thick omelets, Japanese-style rolled omelets, egg ingredients for Tianjin rice bowl, egg soups, egg-drop, quiches, omelets, thin omelets (egg sheets for omurice, thin egg strips), chawanmushi, and steamed egg custard) and foods in which egg white is used as a binding agent (such as fish pastes such as kamaboko, chikuwa, hanpen, datemaki, and fish sausages; processed meats such as hamburgers, meat balls, patties, meat loaves, and minced meat cutlets; and foods obtained by substituting these with vegetable pseudo meats).

In methods for producing these foods, the step 1 can be performed in any stage, among the normal cooking steps performed to cook the foods, in which an egg white protein is not thermally coagulated, and then a normal cooking step of thermally coagulating the egg white protein (step corresponding to the step 2) can be performed.

2. Method of Adjusting Strength of Gel Obtained by Thermal Coagulation of Egg White Protein As described above, the protein deamidase as an active component of the strength-adjusting agent for a gel to be obtained by thermal coagulation of an egg white protein of the present invention can perform adjustment to increase or decrease the strength of a gel obtained by thermal coagulation of an egg white protein. Therefore, the present invention also provides a method for adjusting a strength of a gel obtained by thermal coagulation of an egg white protein, and the method includes a step 1 of treating an egg white protein with a protein deamidase and a step 2 of thermally coagulating the treated protein.

In the method for adjusting a strength of a gel obtained by thermal coagulation of an egg white protein of the present invention, the type and the amount of a component used, the conditions for each step, and the like are as shown in the item "1. Strength-Adjusting Agent for Gel to Be Obtained by Thermal Coagulation of Egg White Protein" above.

3. Method for Producing Material for Gelation

As described above, the protein deamidase can increase or decrease the gel strength of a gel generated by thermal coagulation of an egg white protein and thus can adjust the gel strength, and the egg white protein treated with the protein deamidase can be used as a material for gelation in which a strength of a gel to be obtained by thermal coagulation is adjusted.

Therefore, the present invention also provides a method for producing a material for gelation, and the method includes a step of treating a material containing an egg white protein using a protein deamidase-containing strength-adjusting agent for a gel to be obtained by thermal coagulation of an egg white protein, to obtain a material for gelation in which a strength of a gel to be obtained by thermal coagulation is adjusted.

The protein deamidase-containing strength-adjusting agent for a gel to be obtained by thermal coagulation of an egg white protein is as shown in the item "1. Strength-Adjusting Agent for Gel to Be Obtained by Thermal Coagulation of Egg White Protein" above.

Specific examples of the material containing an egg white protein in the method for producing a material for gelation of the present invention include purified egg white proteins, raw egg white, dried egg white, raw whole eggs, and dried whole eggs.

The amount of the protein deamidase used, the treatment temperature, the treatment time, and the like in the treatment of the material containing an egg white protein are as described in the description of the step 1 in "1-4. Intended Use" in "1. Strength-Adjusting Agent for Gel to Be Obtained by Thermal Coagulation of Egg White Protein" above.

The form of the material for gelation, obtained with the method for producing a material for gelation of the present invention, in which a strength of a gel to be obtained by thermal coagulation is adjusted is not particularly limited as long as the egg white protein is not thermally coagulated. Examples of the form of the material for gelation in which a strength of a gel to be obtained by thermal coagulation is adjusted include forms of liquids and solids (such as frozen products, freeze-dried products, and spray-dried products).

4. Method for Producing Food

The material for gelation in which a strength of a gel to be obtained by thermal coagulation is adjusted can be used for producing various foods. Therefore, the present invention also provides a method for producing a food using the material for gelation in which a strength of a gel to be obtained by thermal coagulation is adjusted.

An example of the method for producing a food of the present invention includes a step of heating and coagulating the material for gelation in which a strength of a gel to be obtained by thermal coagulation is adjusted.

In an example of the method for producing a food, the temperature for heating and coagulating is not particularly limited as long as the egg white protein can be thermally coagulated at the temperature. The temperature is to be appropriately determined according to the type of the egg white protein used as a raw material of the material for gelation, and is, for example, 60° C. or higher, preferably 65° C. or higher, more preferably 70° C. or higher, still more preferably 75° C. or higher, and still even more preferably 78° C. or higher. The upper limit of the treatment temperature range is not particularly limited, and can be appropriately determined by those skilled in the art according to the form of a food to be produced.

Examples of the food obtained by an example of the method for producing a food include cooked egg foods, more specifically, boiled eggs, hot-spring eggs, poached eggs, scrambled eggs, thick omelets, Japanese-style rolled omelets, egg ingredients for Tianjin rice bowl, egg soups, egg-drop, quiches, omelets, thin omelets (egg sheets for omurice, thin egg strips), chawanmushi, and steamed egg custard.

Another example of the method for producing a food of the present invention includes a step of preparing a mixture of the material for gelation in which a strength of a gel to be obtained by thermal coagulation is adjusted and another food material and a step of heating the mixture at a temperature at which the material for gelation is coagulated by heating.

In another example of the method for producing a food, another food material to be used and the heating condition can be appropriately determined by those skilled in the art according to the form of the food to be produced as long as the egg white protein can be thermally coagulated at the temperature.

Examples of the food obtained by another example of the method for producing a food include foods in which egg white is used as a binding agent, more specifically, fish pastes such as kamaboko, chikuwa, hanpen, datemaki, and fish sausages; processed meats such as hamburgers, meat balls, patties, meat loaves, and minced meat cutlets; and foods obtained by substituting these with vegetable pseudo meats.

EXAMPLES

Hereinafter, the present invention will be specifically described with reference to Examples, but the present invention is not to be construed as being limited to the following Examples.

Used Enzyme

As a protein deamidase, PG-500 (Protein-glutaminase "Amann" 500: protein-glutaminase derived from *Chryseobacterium proteolyticum*, hereinafter, also referred to as "PG") was used.

The protein deamidase activity value was measured with the following method.

To 1 mL of a 0.2 M phosphate buffer (pH 6.5) containing 30 mM Z-Gln-Gly, 0.1 mL of a sample solution containing a protein deamidase was added, the mixture was allowed to stand at 37° C. for 10 minutes, and then 1 mL of a 0.4 M TCA solution was added to stop the reaction. To 1 mL of a 0.2 M phosphate buffer (pH 6.5) containing mM Z-Gln-Gly, 1 mL of a 0.4 M TCA reagent was added, 0.1 mL of a sample solution containing a protein deamidase was further added, and the mixture was allowed to stand at 37° C. for 10 minutes as a blank.

The solution obtained above was measured using Ammonia Test Wako (FUJIFILM Wako Pure Chemical Corporation) to determine the amount of ammonia generated in the reaction liquid. A calibration curve representing the relationship between the ammonia concentration and the absorbance (630 nm) was prepared using an ammonia standard solution (ammonium chloride), and from the calibration curve, the ammonia concentration in the reaction liquid was determined.

The amount of the enzyme that produces 1 μmol of ammonia per minute was defined as 1 unit (1 U), and the activity of the protein deamidase was calculated from the following formula. In the formula, the reaction liquid amount is 2.1, the enzyme solution amount is 0.1, and Df is a dilution rate of the enzyme solution. Furthermore, 17.03 is a molecular weight of ammonia.

$$\text{Protein deamidase activity (U/mL)} = \text{ammonia concentration in reaction liquid (mg/L)} \times (1/17.03) \times (\text{reaction liquid amount/enzyme solution amount}) \times (1/10) \times Df \qquad \text{[Math. 1]}$$

Test Example 1

Into a 50 mL tube, 0.5 g of egg albumin (FUJIFILM Wako Pure Chemical Corporation) was weighed out and put, and 10 mL of a 50 mM phosphate buffer (pH 7.0) was added (dilution rate of egg albumin 5 w/v %). PG was added in an amount of 2.5 U, 25 U, or 250 U with respect to 1 g of egg albumin as a substrate, and the mixture was allowed to stand at 40° C. for 2 hours or 24 hours for reaction. The entire reaction liquid was transferred to a petri dish and heated at 80° C. for 1 hour, and thus thermally coagulated. The gel obtained by thermal coagulation of egg albumin was measured using a rheometer (manufactured by SUN SCIEN-TIFIC CO., LTD.) to determine the gel strength. A gel obtained by thermal coagulation of egg albumin was obtained in the same manner except that no PG was added, the gel strength of this gel was regarded as 100%, and the gel strength determined above was converted to a relative amount (%) with respect to a gel strength of 100%. FIG. 1 shows the results.

As shown in FIG. 1, in the case of adding 2.5 U of PG with respect to 1 g of egg albumin, the gel strength of the gel obtained by thermal coagulation was increased. Meanwhile, in the case of adding 25 U or 250 U of PG with respect to 1 g of egg albumin, the gel strength of the gel obtained by thermal coagulation was decreased.

Test Example 2

Figure 2:
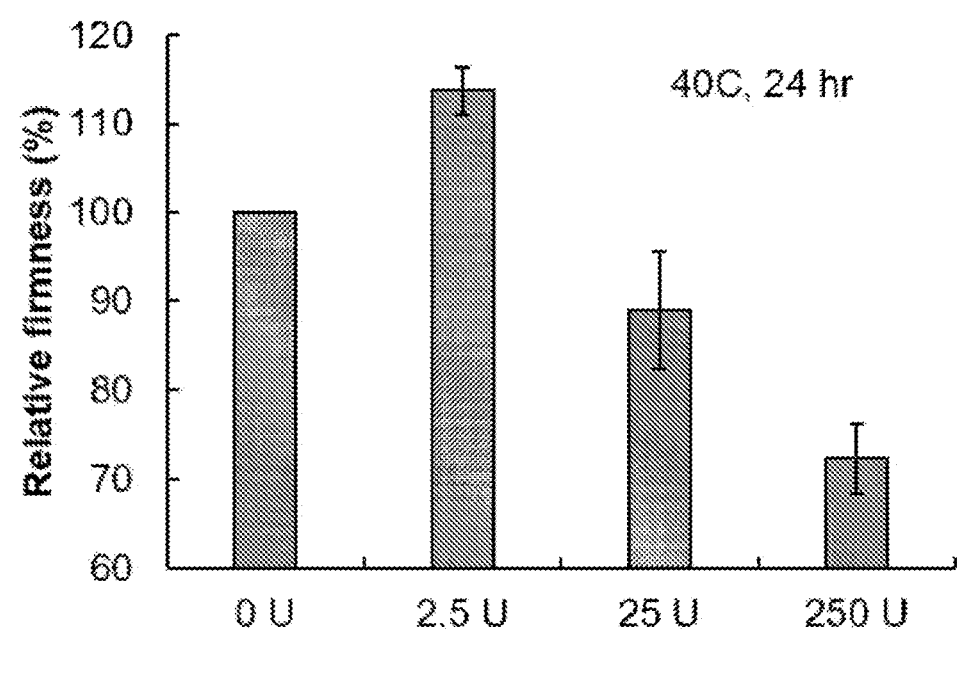
FIG. 2 shows results of adjusting the strength of a gel obtained by thermal coagulation of an egg albumin diluted at a dilution rate of 10 w/v % and subjected to a PG treatment.

A relative amount (%) of the gel strength of a gel obtained by thermal coagulation of egg albumin was obtained in the same manner as in Test Example 1 except that 1.0 g of egg albumin was weighed out and put into a 50 mL tube and 10 mL of a 50 mM phosphate buffer (pH 7.0) was added to dilute the egg albumin at a dilution rate of 10 w/v %, and that the PG treatment time was set to 24 hours. FIG. 2 shows the results.

As shown in FIG. 2, in the case of adding 2.5 U of PG with respect to 1 g of egg albumin, the gel strength of the gel obtained by thermal coagulation was increased. Meanwhile, in the case of adding 25 U or 250 U of PG with respect to 1 g of egg albumin, the gel strength of the gel obtained by thermal coagulation was decreased.

The invention claimed is:

1. A method for adjusting a strength of a gel obtained by thermal coagulation of an egg white protein, the method comprising:
   treating an egg white protein with a protein glutaminase; and
   thermally coagulating the egg white protein treated.

2. The method according to claim 1, wherein the protein deamidase is used in an amount of 0.1 to 19 U with respect to 1 g of the egg white protein.

3. The method according to claim 1, wherein the protein deamidase is used in an amount of 20 U or more with respect to 1 g of the egg white protein.

4. The method according to claim 1, wherein the gel is in a food.

* * * * *